US00PP22691P2

(12) United States Plant Patent
Kordes

(10) Patent No.: US PP22,691 P2
(45) Date of Patent: May 1, 2012

(54) FLORIBUNDA ROSE PLANT NAMED 'KORVODACOM'

(50) Latin Name: *Rosa hybrida*
Varietal Denomination: KORvodacom

(75) Inventor: Tim-Hermann Kordes, Klein Offenseth-Sparrieshoop (DE)

(73) Assignee: W. Kordes Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/925,197

(22) Filed: Oct. 15, 2010

(51) Int. Cl.
*A01H 5/00* (2006.01)

(52) U.S. Cl. ..... Plt./141

(58) Field of Classification Search ..... Plt./102, Plt./107, 141, 148, 149
See application file for complete search history.

*Primary Examiner* — Kent L Bell

(57) ABSTRACT

A new and distinct variety of rose with long lasting, novel lavender flowers, and attractive foliage with good disease resistance. It exhibits moderate growth and an upright habit with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORvodacom'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1997. The crossing was between an 'un-named seedling' and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORvodacom'.

SUMMARY OF THE INVENTION

The new rose plant may be distinguished from its seed parent, an 'un-named seedling', by the following combination of characteristics:

1. The flower size of 'KORvodacom' is medium while the flower size of the seed parent is small.
2. The petal count of 'KORvodacom' is very double while the petal count of the seed parent is semi-double.

The new rose plant may be distinguished from its pollen parent, an 'un-named seedling' by the following combination of characteristics:

1. The petal count of 'KORvodacom' is very double while the petal count of the pollen parent is only double 2. The disease resistance of 'KORvodacom' is good while the disease resistance of the pollen parent is low.

The objective of the hybridization was to create a new and distinct rose plant with unique qualities, such as:

1. Uniform growth and flowering;
2. Abundant attractive, lavender recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORvodacom' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORvodacom' was selected in May, 1998 from the seedling beds to be asexually propagated for further evaluation. The first asexual propagation of 'KORvodacom' was done by budding to seedling understocks in July, 1998 at the inventor's nursery in Offenseth-Sparrieshoop, Germany.

This initial and other subsequent propagations conducted in controlled environments demonstrate that 'KORvodacom' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORvodacom'.

DETAILED BOTANICAL DESCRIPTION

The following is a description of 'KORvodacom', as observed growing in September, 2011 in a nursery in Jackson County, Oreg. on plants of 1 year of age. Color references are made using The Royal Horticultural Society (London, England) Colour Chart, 2001 except where common terms of color are used.

For a comparison, several physical characteristics of the rose variety 'KORtutu', a rose variety from the same inventor described and illustrated in U.S. Plant patent application Ser. No. 12/925,240 and filed on Oct. 14, 2010 are compared to 'KORvodacom' in Chart 1.

CHART 1

| Characteristic | 'KORvodacom' | 'KORtutu' |
|---|---|---|
| Flower Color: | Lavender. | Dark Red. |
| Flower bud size upon opening: | 20 mm (1) × 15 mm in diameter. | 40 mm (1) × 25 mm in diameter. |
| Flower Fragrance: | None. | Light. |

Parents:

*Seed parent.*—An 'un-named seedling'.

*Pollen parent.*—An 'un-named seedling'.

Classification:

*Botanical classification.*—*Rosa hybrida* 'KORvodacom'.

*Commercial classification.*—Floribunda rose.

FLOWER AND FLOWER BUD

Blooming habit: Recurrent.

Flower bud:

*Size.*—Average 20 mm long×15 mm in diameter from base of receptacle to end of bud.

*Bud form.*—Short. Pointed ovoid.

*Bud color.*—As sepals unfold, Red-Purple Group 70A and 70B. At ¼ opening, upper surface of petal is Red-Purple Group 72B and the lower surface is Red-Purple Group 70B.

*Sepals.*—Color: Upper surface: Yellow-Green Group 147D. Lower surface: Yellow-Green Group 144A. Size: Average 25-30 mm (l)×7-10 mm (w). Shape: Strong foliaceous appendages on two of the five sepals. Apex: Apiculate. Base: Flat at union with receptacle. Quantity: Five. Surface texture: Upper surface: pubescent. Lower surface: glabrous with light pubescence and occasional stipitate glands. Margins: Pubescent with fine hairs and stipitate glands.

Receptacle:

*Surface.*—Glabrous.

*Color.*—Yellow-Green Group 144B.

*Shape.*—Pear-shaped.

*Size.*—14 mm (h)×10 mm (w).

Peduncle:

*Surface.*—Smooth.

*Length.*—60 to 80 mm average length.

*Diameter.*—1 to 2 mm average diameter.

*Color.*—Yellow-Green Group 144A.

*Strength.*—Moderately strong.

*Borne.*—Multiple flower buds per stem, generally 1 to 5.

Flower bloom:

*Fragrance.*—None.

*Duration.*—On the plant approximately 5 to 6 days. As a cut flower, 4 to 5 days. Senesced petals drop away cleanly.

*Size.*—Medium for a floribunda rose. When open, the average flower diameter is 60-80 mm and the average flower height is 30 to 40 mm.

*Form.*—Shape of flower when viewed from the side: Upon opening, upper part: Flat. Upon opening, lower part: Flat. Open flower, upper part: Flattened convex. Open flower, lower part: Concave.

Color:

*Upon opening, petals.*—Outermost petals: Outer Side: Red-Purple Group 72B. Inner Side: Red-Purple Group 72A. Innermost petals: Outer Side: Purple Group N77B. Inner Side: Red-Purple Group 72A.

*Upon opening, basal petal spots.*—Basal petal spot, outermost petals: Outer Side: Purple Group 77D. Inner Side: Purple Group 77C. Basal petal spot, innermost petals: Outer Side: Green-White Group 157B. Inner Side: Purple Group 75D.

*After opening, petals.*—Outermost petals: Outer Side: Purple Group N78D. Inner Side: Purple Group 77B. Innermost petals: Outer Side: Purple Group N78D. Inner Side: Purple Group 77B.

*After opening, basal petal spots.*—Basal petal spot, outermost petals: Outer Side: White Group 155D. Inner Side: White Group 155B. Basal petal spot, innermost petals: Outer Side: Yellow Group 11C. Inner Side: Yellow Group 11A.

General tonality: On open flower Purple Group 77B. No change in the general tonality at the end of the 3$^{rd}$ day. Afterwards, general tonality is Purple Group 77D.

Petals:

*Petal count.*—Very Double. Average range is approximately 75 petals under normal conditions.

*Petal reflex.*—Moderately reflexed.

*Petal edge.*—Ruffled.

*Petal shape.*—Deltoid. Apex shape is round. Shape of base is acute.

*Petal size.*—Average of 40 mm (l)×30 mm (w).

*Thickness.*—Average.

*Petal arrangement.*—Not formal.

Petaloids:

*Petaloid count.*—Average of 8-15 per flower.

*Petaloid size.*—Petaloids are 7 mm (l) and 3 mm (w).

*Petaloid color.*—Color of inner side is Purple Group 77B. Color of outer side is Marginal zone, Purple Group 77C, Middle zone White Group N55C and basal zone Purple Group 77B.

*Petaloid texture.*—Thin.

*Margins.*—Undulated.

*Petaloid shape.*—Most commonly deltoid, with some petaloids highly irregular. Apex: Deltoid. Base: Pointed.

Reproductive organs:

*Pistils.*—Approximately 25 present. Stigmas: Location: Slightly inferior in position to anthers. Color: Yellow-Orange Group 22A. Styles: Length: About 7 mm long. Color: Purple Group 75C.

*Stamens.*—Approximately 50 on average and regularly arranged. Anthers: Size: Average 0.5 (l). Pollen: Generally present. Color: Greyed-Brown Group N199C. Filaments: Color: Yellow Group 11D. Length: About 6 mm.

THE PLANT

Growth: Moderate growth

Plant habit: Upright, yet bushy habit. When grown as a budded field grown plant, the average plant height is 80 cm and the average plant width is 50 cm.

Stems:

*Stem color.*—Juvenile wood: Yellow-Green Group 144A. Mature wood: Yellow-Green Group 144A.

*Stem surface.*—Juvenile wood: Smooth. Mature wood: Smooth.

Prickles: Present.

*Incidence.*—Average of 10-14 per each 10 cm of stem.

*Size.*—Average length: 6 mm.

*Color.*—Immature prickles: Green-Yellow Group 162A. Mature prickles: Greyed-Red Group 182A. Senescing to Greyed-Brown Group 199A.

*Shape.*—Concave.

*Anthocyanin.*—Anthocyanin color of Greyed-Purple Group 187C present on thorn tips.

Leaves and leaflets: Normally 5 to 7 leaflets on normal leaves in middle of the stem.

*Venation pattern.*—Pyramidal net pattern.

*Leaf size.*—90 to 110 mm (l)×60 to 70 mm (w).

*Abundance.*—Average.

*Texture.*—Leathery. Upper side of leaflet: is glossy and smooth. Under side of leaflet: is matte and rough.

*Color, mature foliage.*—Upper Leaf Surface: Green Group 137A. Lower Leaf Surface: Green Group 137C.

*Color, juvenile foliage.*—Upper Leaf Surface: Yellow-Green Group 144A. Lower Leaf Surface: Yellow-Green Group 144B.

*Anthocyanin intonation.*—Present on upper and lower surfaces of leaflets. Mottled colors of Greyed-Purple Group 183B and 183D across leaflet surface.

Stipules:

*Size.*—15-20 mm long and 3-4 mm from tips of distils.

*Stipule color.*—Green Group 137A.

*Shape.*—Apex: Apiculate. Base: Winged.

Petiole:

*Length.*—Average 25 mm.

*Diameter.*—Average 1 mm.

*Petiole color.*—Yellow-Green Group 144A.

*Underneath.*—Many small prickles.

*Margins.*—With stipitate glands.

*Anthocyanin.*—Greyed-Purple Group 184B.

Petiole rachis:

*Length.*—Average 55-65 mm.

*Diameter.*—Average 1-2 mm.

*Color.*—Yellow-Green Group 144A.

*Margins.*—Stipitate glands present.

*Prickles.*—Small prickles on lower surface.

*Stipitate glands.*—Few stipitate glands on margins.

Leaflets:

*Size.*—Average size of the terminal leaflet is 85 mm (l)×60 mm (w).

*Shape.*—Base: Ovate. Apex: Acute.

*Margins.*—Serrated.

*Surface.*—Upper: Moderately glossy. Lower: Matte.

*Texture.*—Leathery.

*Arrangement.*—Odd pinnate.

*Venation.*—Reticulate.

Hips/seed formation: None observed.

Winter hardiness: To date, the variety has been grown successfully in USDA Zones 5-9.

Disease resistance: Good resistance to Powdery mildew (*Sphaerotheca pannosa*), blackspot (*Diplocarpon rosae*), and rust (*Phragmidium* sp) diseases under normal growing conditions.

I claim:

1. A new and distinct variety of rose plant, as described and illustrated herein.

* * * * *

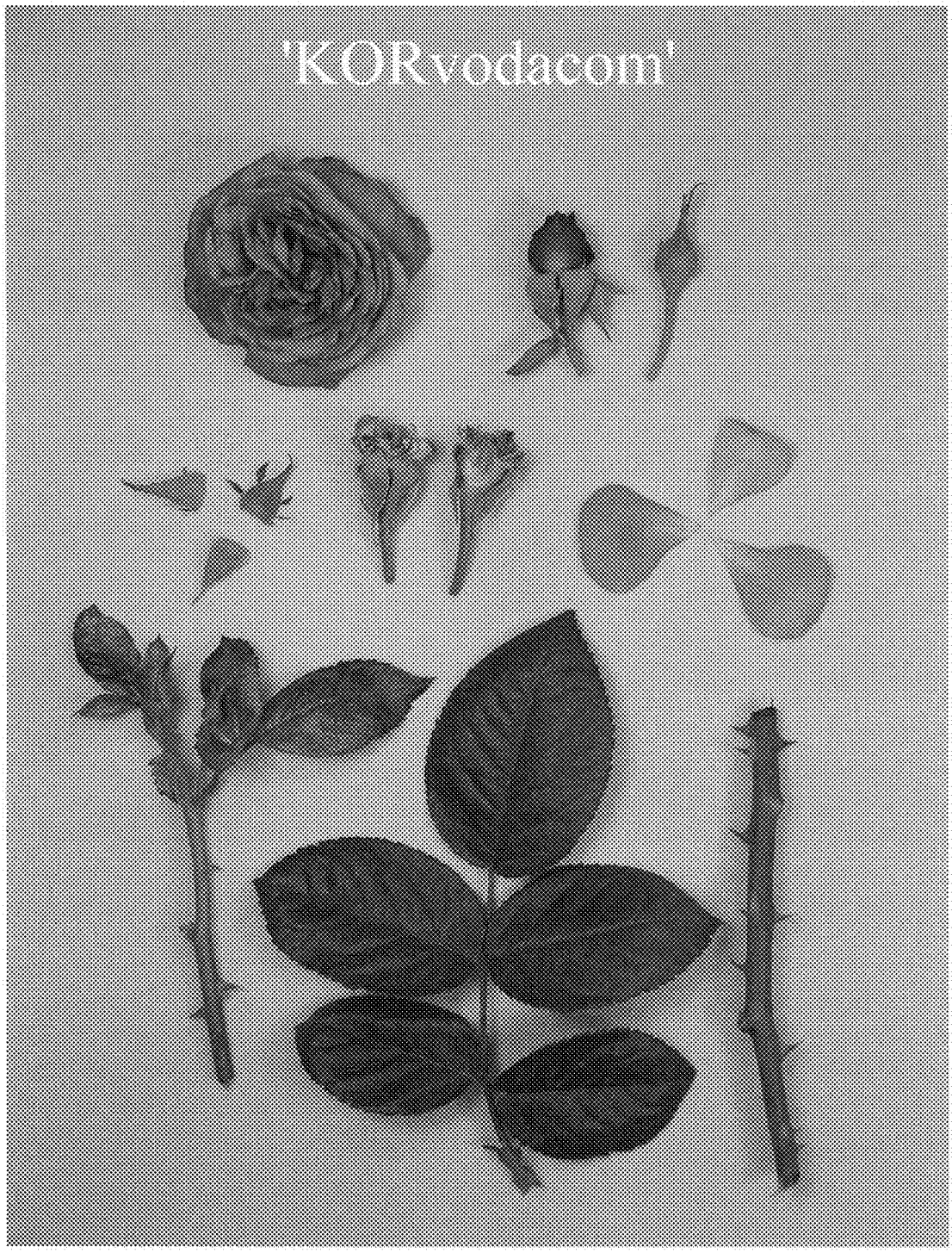
'KORvodacom'